(12) United States Patent
Yang et al.

(10) Patent No.: US 12,144,683 B2
(45) Date of Patent: Nov. 19, 2024

(54) ULTRASOUND DIAGNOSIS APPARATUS AND OPERATING METHOD THEREOF FOR DISPLAYING ULTRASOUND ELASTICITY IMAGES

(71) Applicant: SAMSUNG MEDISON CO., LTD., Hongcheon-gun (KR)

(72) Inventors: Sunmo Yang, Seongnam-si (KR); Jihun Kim, Seongnam-si (KR); Wonik Heo, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 16/986,681

(22) Filed: Aug. 6, 2020

(65) Prior Publication Data
US 2021/0219959 A1   Jul. 22, 2021

(30) Foreign Application Priority Data
Jan. 17, 2020   (KR) .................. 10-2020-0006749

(51) Int. Cl.
  *A61B 8/00*   (2006.01)
  *A61B 8/08*   (2006.01)
(52) U.S. Cl.
  CPC ............. *A61B 8/485* (2013.01); *A61B 8/461* (2013.01); *A61B 8/468* (2013.01); *A61B 8/5207* (2013.01)
(58) Field of Classification Search
  CPC ......... A61B 8/485; A61B 8/461; A61B 8/468; A61B 8/5207; A61B 8/463; A61B 8/469; A61B 8/5223; A61B 8/5253; A61B 8/465
  See application file for complete search history.

(56) References Cited

U.S. PATENT DOCUMENTS

| 6,786,869 B2 | 9/2004 | Hashimoto |
| 10,390,797 B2 | 8/2019 | Shi et al. |

(Continued)

FOREIGN PATENT DOCUMENTS

| CN | 110573088 A | 12/2019 |
| EP | 3 320 850 A1 | 5/2018 |

(Continued)

OTHER PUBLICATIONS

Communication dated Feb. 8, 2021 in by the European Patent Office in corresponding European Patent Application No. 20194063.2.

(Continued)

*Primary Examiner* — Joel Lamprecht
*Assistant Examiner* — James F McDonald, III
(74) *Attorney, Agent, or Firm* — Sughrue Mion, PLLC

(57) ABSTRACT

An ultrasound diagnosis apparatus includes: a display; a memory storing one or more instructions; and a processor configured to execute the one or more instructions stored in the memory to: acquire first elasticity data with respect to a first area of an object; generate a first elasticity image based on the first elasticity data; acquire, based on the first elasticity data, first and second elasticity values respectively corresponding to first and second regions of interest included in the first area; control the display to display the acquired first and second elasticity values; and control the display to display, when the first elasticity value is selected, the first elasticity image and the first region of interest corresponding to the first elasticity value.

13 Claims, 12 Drawing Sheets

(56) References Cited

U.S. PATENT DOCUMENTS

| | | | |
|---|---|---|---|
| 2010/0331694 A1 | 12/2010 | Waki | |
| 2012/0123263 A1 | 5/2012 | Osaka et al. | |
| 2014/0180177 A1* | 6/2014 | Rothberg | A61B 8/4494 601/3 |
| 2015/0141822 A1* | 5/2015 | Miyauchi | A61B 8/485 600/438 |
| 2016/0287215 A1* | 10/2016 | Choi | A61B 8/5207 |
| 2017/0340312 A1 | 11/2017 | Shiki | |
| 2017/0360408 A1 | 12/2017 | Toji | |
| 2018/0132831 A1* | 5/2018 | Yang | A61B 8/54 |
| 2019/0209121 A1* | 7/2019 | Miyachi | A61B 8/0858 |
| 2019/0254629 A1 | 8/2019 | Li et al. | |
| 2019/0388061 A1* | 12/2019 | Yang | A61B 8/5223 |
| 2021/0038195 A1* | 2/2021 | Li | A61B 8/5246 |

FOREIGN PATENT DOCUMENTS

| | | | | |
|---|---|---|---|---|
| JP | 2004-148015 A | 5/2004 | | |
| KR | 10-2016-0114487 A | 10/2016 | | |
| KR | 10-2018-0054360 A | 5/2018 | | |
| KR | 10-2018-0087698 A | 8/2018 | | |
| WO | WO-2019205167 A1 * | 10/2019 | | A61B 8/085 |
| WO | WO-2019211175 A1 * | 11/2019 | | A61B 18/1492 |
| WO | WO-2020002445 A1 * | 1/2020 | | A61B 8/461 |

OTHER PUBLICATIONS

Office Action dated Feb. 13, 2024, issued by the European Patent Office in European Application No. 20 194 063.2.

Communication dated Sep. 7, 2023 issued by the European Patent Office in Application No. 20194063.2.

Communication issued Aug. 19, 2024 by the Korean Intellectual Property Office in Korean Patent Application No. 10-2020-0006749.

* cited by examiner

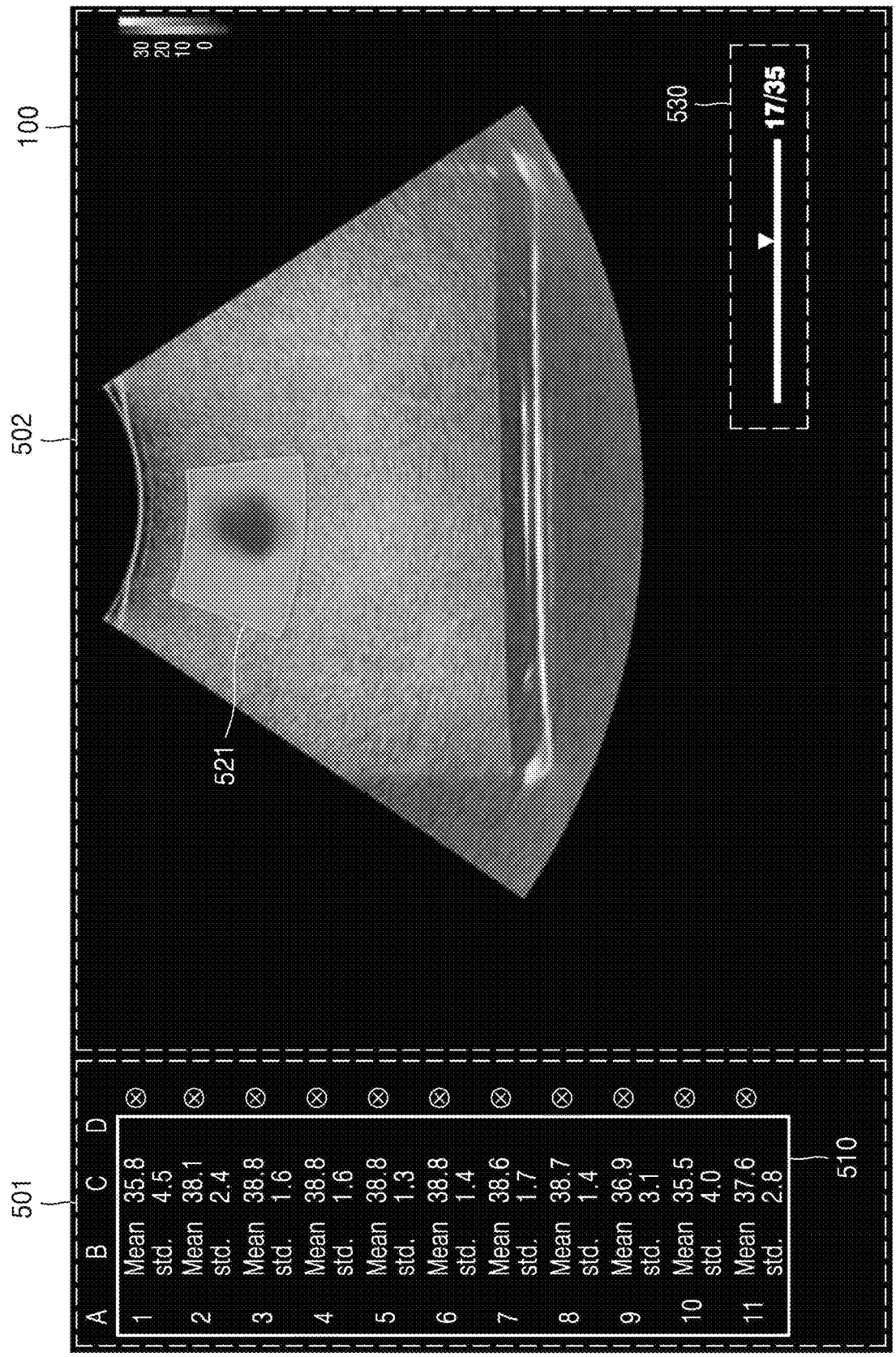

ULTRASOUND DIAGNOSIS APPARATUS AND OPERATING METHOD THEREOF FOR DISPLAYING ULTRASOUND ELASTICITY IMAGES

CROSS-REFERENCE TO RELATED APPLICATION(S)

This application is based on and claims priority under 35 U.S.C. § 119 to Korean Patent Application No. 10-2020-0006749, filed on Jan. 17, 2020, in the Korean Intellectual Property Office, the disclosure of which is incorporated by reference herein in its entirety.

BACKGROUND

1. Field

Various embodiments relate to ultrasound diagnosis apparatuses and operating methods thereof, and more particularly, to ultrasound diagnosis apparatuses and operating methods thereof for displaying an ultrasound image of an object to correspond to measurement data regarding the object.

2. Description of Related Art

Recently, in the medical field, various types of medical imaging apparatuses have been widely used to visualize and acquire information about living tissue of a human body for early diagnosis or surgery with regard to various diseases. Representative examples of these medical imaging apparatuses may include an ultrasound diagnosis apparatus, a computed tomography (CT) apparatus, and a magnetic resonance imaging (MRI) apparatus.

Ultrasound diagnosis apparatuses transmit ultrasound signals generated by transducers of a probe to an object and receive information of echo signals reflected from the object, thereby obtaining an image of an internal part of the object. In particular, ultrasound diagnosis apparatuses are used for medical purposes including observing an internal area of an object, detecting foreign substances, and assessing injuries. Such ultrasound diagnosis apparatuses exhibit high stability, display images in real-time, and are safe due to lack of radiation exposure, as compared to diagnostic X-ray apparatuses, and therefore, ultrasound diagnosis apparatuses have been widely used together with other types of imaging diagnostic apparatuses.

In an elasticity measurement mode in which an elasticity value is measured based on an elasticity image of an object, after measuring a plurality of elasticity values, a user is inconvenienced in having to individually examine a plurality of elasticity images in order to identify an elasticity value selected among the measured elasticity values and an elasticity image corresponding to the selected elasticity value.

SUMMARY

Provided are ultrasound diagnosis apparatuses and operating methods thereof, which are capable of acquiring ultrasound data with respect to an object and displaying an ultrasound image generated based on the ultrasound data correspond to a data value measured based on the ultrasound data Additional aspects will be set forth in part in the description which follows and, in part, will be apparent from the description, or may be learned by practice of the presented embodiments of the disclosure.

In accordance with an aspect of the disclosure, an ultrasound diagnosis apparatus includes: a display; a memory storing one or more instructions; and a processor configured to execute the one or more instructions stored in the memory to: acquire first elasticity data with respect to a first area of an object; generate a first elasticity image based on the first elasticity data; acquire, based on the first elasticity data, first and second elasticity values respectively corresponding to first and second regions of interest included in the first area; control the display to display the acquired first and second elasticity values; and control the display to display, when the first elasticity value is selected, the first elasticity image and the first region of interest corresponding to the first elasticity value.

The processor may be further configured to execute the one or more instructions to: acquire second elasticity data with respect to a second area of the object; generate a second elasticity image based on the second elasticity data; acquire, based on the second elasticity data, third and fourth elasticity values respectively corresponding to third and fourth regions of interest included in the second area; control the display to display the acquired third and fourth elasticity values; and when the third elasticity value is selected, control the display to display the second elasticity image and the third region of interest corresponding to the third elasticity value.

The processor may be further configured to execute the one or more instructions to: control the display to display, in a first region of the display, a list including first through fourth items respectively corresponding to the first through fourth elasticity values; and when the first item is selected from the list, control the display to display the first elasticity image having the first region of interest shown therein in a second region of the display.

The processor may be further configured to execute the one or more instructions to: determine the first and second elasticity values acquired based on the first elasticity data as a first group; determine the third and fourth elasticity values acquired based on the second elasticity data as a second group; and control the display to display the corresponding elasticity values for each of the first and second groups.

The processor may be further configured to execute the one or more instructions to, when the first group is selected, control the display to display an elasticity image corresponding to the first group to be distinguished from an elasticity image corresponding to the second group.

The processor may be further configured to execute the one or more instructions to: control the display to display a thumbnail list including elasticity images corresponding to the first group and elasticity images corresponding to the second group; and when the first group is selected, control the display to highlight and display the elasticity images corresponding to the first group in the thumbnail list.

The list may further include a fifth item corresponding to a fifth elasticity value, and the processor may be further configured to execute the one or more instructions to, when the fifth item is selected from the list and an elasticity image corresponding to the fifth elasticity value is not stored, control the display to display a message indicating that there is no corresponding elasticity image.

The processor may be further configured to execute the one or more instructions to control the display to display, in the list, an item for which a corresponding elasticity image is stored to be distinguished from an item for which a corresponding elasticity image is not stored.

The ultrasound diagnosis apparatus may further include a user input interface configured to receive a user input for selecting the first elasticity value.

In accordance with another aspect of the disclosure, an operating method of an ultrasound diagnosis apparatus includes: acquiring first elasticity data with respect to a first area of an object; generating a first elasticity image based on the first elasticity data; acquiring, based on the first elasticity data, first and second elasticity values respectively corresponding to first and second regions of interest included in the first area; displaying the acquired first and second elasticity values; and displaying, when the first elasticity value is selected, the first elasticity image and the first region of interest corresponding to the first elasticity value.

BRIEF DESCRIPTION OF THE DRAWINGS

These and/or other aspects will become apparent and more readily appreciated from the following description of the embodiments, taken in conjunction with the accompanying drawings in which:

FIGS. 5A through 5C are reference diagrams for describing a method by which an ultrasound diagnosis apparatus provides an elasticity value and an elasticity image corresponding to the elasticity value, according to an embodiment;

DETAILED DESCRIPTION

Figure 1:
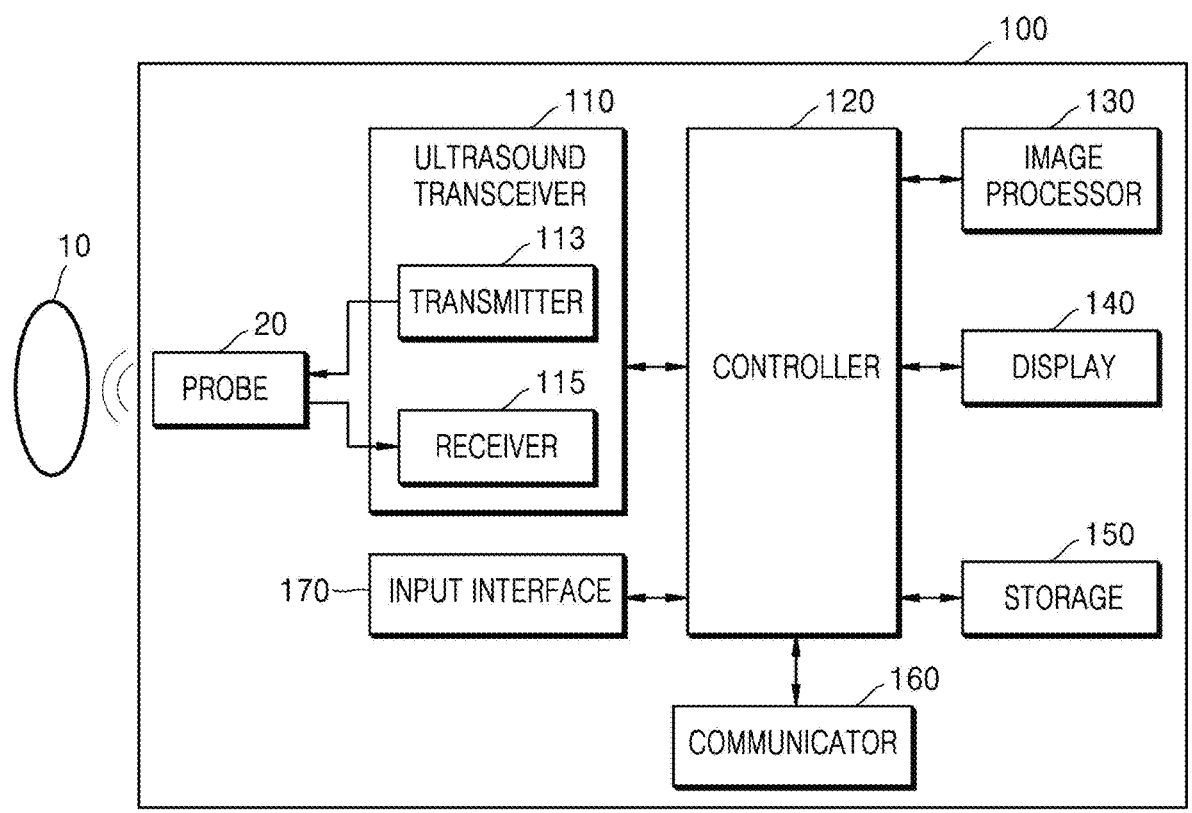
FIG. 1 is a block diagram illustrating an ultrasound diagnosis apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

As used herein, the term "and/or" includes any and all combinations of one or more of the associated listed items. Expressions such as "at least one of," when preceding a list of elements, modify the entire list of elements and do not modify the individual elements of the list.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2C:
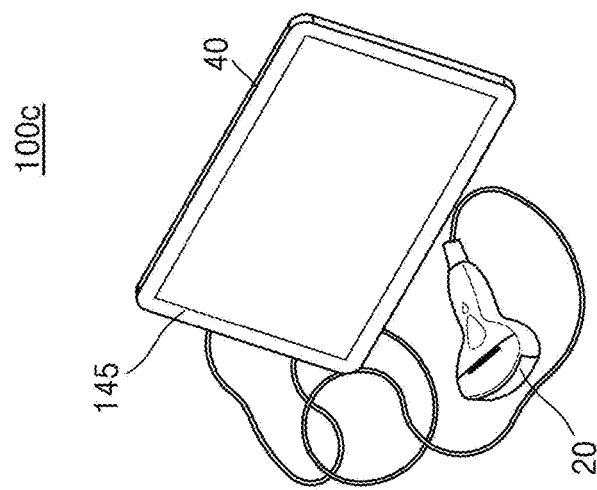
FIGS. 2A, 2B, and 2C are diagrams respectively illustrating an ultrasound diagnosis apparatus according to an exemplary embodiment.
Figure 2B:
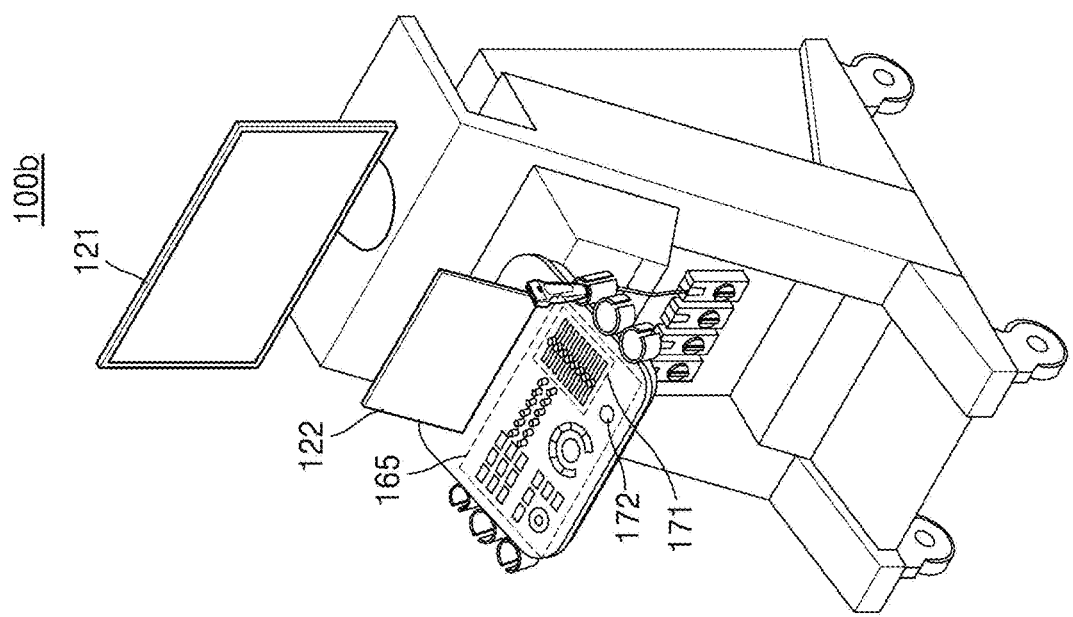
Figure 2A:
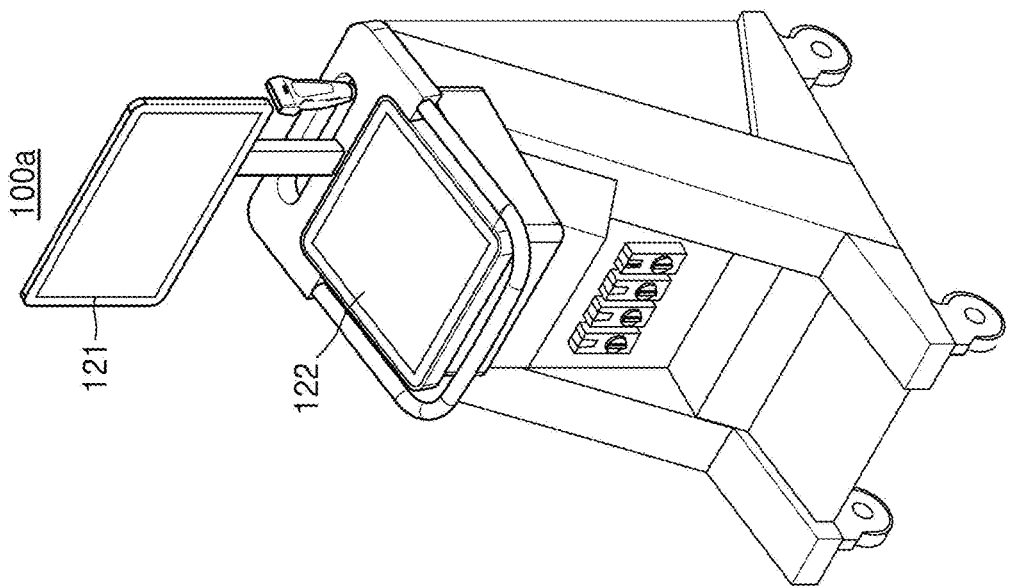

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
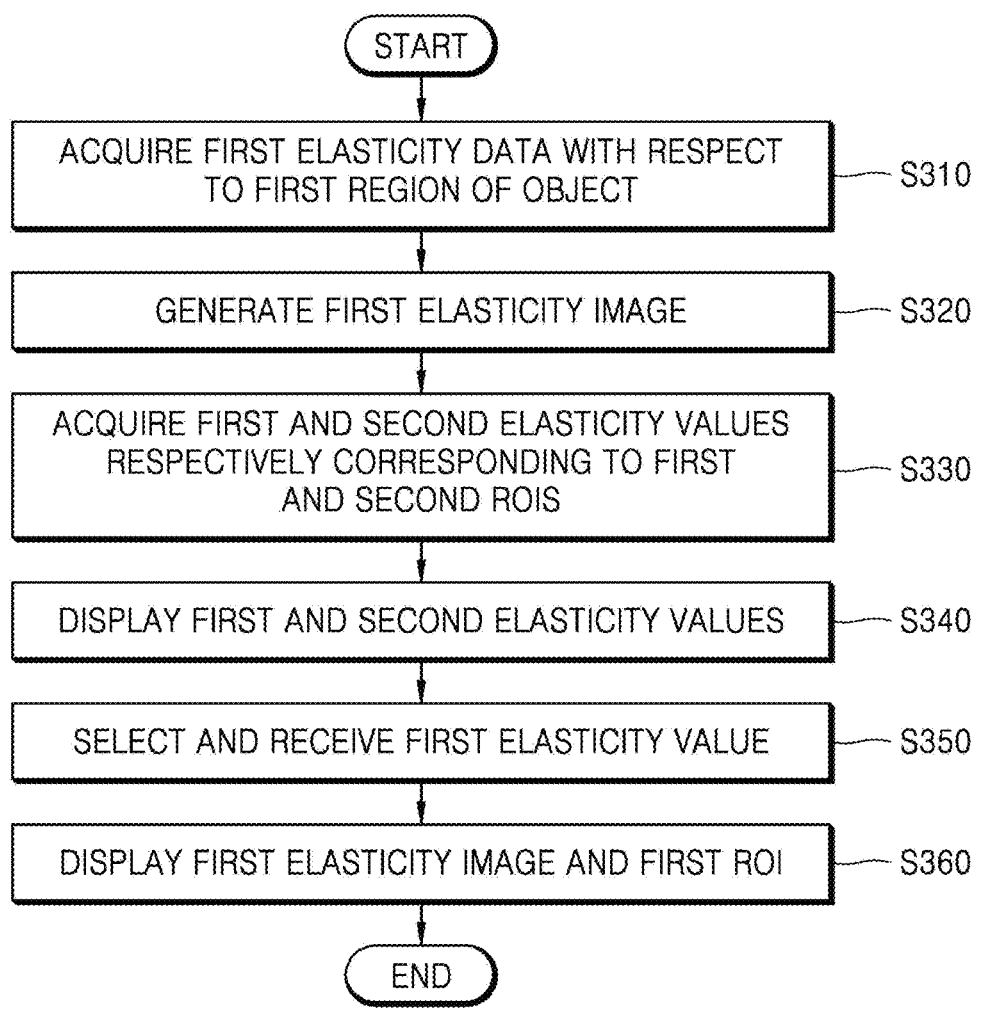
FIG. 3 is a flowchart of an operating method of an ultrasound diagnosis apparatus, according to an embodiment.

FIG. 3 is a flowchart of an operating method of the ultrasound diagnosis apparatus 100, according to an embodiment.

According to an embodiment, the ultrasound diagnosis apparatus 100 may transmit ultrasound signals to an object and receive echo signals generated in response to the transmitted ultrasound signals, thereby acquiring ultrasound data with respect to the object.

For example, the ultrasound diagnosis apparatus 100 may acquire brightness (B)-mode data with respect to the object, generate a B-mode ultrasound image based on the B-mode data, and display the generated B-mode ultrasound image. The ultrasound diagnosis apparatus 100 may extract B-mode components from ultrasound data and generate a B-mode ultrasound image in which signal intensities are represented as brightness levels based on the extracted B-mode components.

According to an embodiment, a first area from which elasticity data is to be acquired may be set in a B-mode image, and a position, a size, and a shape of the first area may be set variously. For example, the ultrasound diagnosis apparatus 100 may receive a user input of setting a first area from which elasticity data is to be acquired and set the first area based on the user input.

According to an embodiment, the ultrasound diagnosis apparatus 100 may acquire first elasticity data with respect to a first area of an object (S310).

The ultrasound diagnosis apparatus 100 may transmit an ultrasound signal for pushing a region (first area) of the object and induce a displacement of internal tissue of the object. A displacement of tissue may be created by a shear wave induced in the tissue of the object by an ultrasound signal. According to an embodiment, an ultrasound signal for inducing a shear wave may be an acoustic radiation force impulse. A shear wave may be induced by an ARFI in tissue of the object to cause a shear wave displacement.

The ultrasound diagnosis apparatus 100 may detect the shear wave displacement caused by the induced shear wave and acquire elasticity data with respect to the object.

According to an embodiment, the ultrasound diagnosis apparatus 100 may generate a first elasticity image based on the first elasticity data (S320).

In this case, the first elasticity image may be an image displayed in different colors according to a plurality of elasticity values corresponding to a plurality of points included in the first area. For example, a point such as a tumor that is hard and has a low elasticity value may appear red while a point that is relatively soft tissue and has a high elasticity value may appear blue.

According to an embodiment, the ultrasound diagnosis apparatus 100 may display a first elasticity image. For example, the ultrasound diagnosis apparatus 100 may display an obtained elasticity image to overlap a B-mode image. However, embodiments are not limited thereto, and the ultrasound diagnosis apparatus 100 may display only an elasticity image, or display an elasticity image and a B mode image in separate regions of a display of the ultrasound diagnosis apparatus 100.

According to an embodiment, the ultrasound diagnosis apparatus 100 may determine, in the first area, a first region of interest (ROI) and a second ROI where elasticity values are to be acquired. For example, the ultrasound diagnosis apparatus 100 may set positions, sizes, shapes, etc., of the first and second ROIs based on a user input.

When the first and second ROIs are set, the ultrasound diagnosis apparatus 100 may acquire a first elasticity value corresponding to the first ROI and a second elasticity value corresponding to the second ROI (S330). In this case, the first and second elasticity values may be acquired based on the first elasticity data. Furthermore, the first elasticity value may include a mean value, a standard deviation, and a confidence level of elasticity values respectively corresponding to a plurality of points included in the first ROI, and the second elasticity value may include a mean value, a standard deviation, and a confidence level of elasticity values corresponding to a plurality of points included in the second ROI. However, embodiments are not limited thereto.

Furthermore, after the first elasticity value is acquired, the ultrasound diagnosis apparatus 100 may store the first elasticity value to correspond to the first elasticity image corresponding to the first elasticity value and an indicator indicating the first ROI.

According to an embodiment, the ultrasound diagnosis apparatus 100 may display the first and second elasticity values (S340). For example, the ultrasound diagnosis apparatus 100 may display an elasticity value list including items respectively corresponding to the first and second elasticity values.

When the first elasticity value is selected (S350), the ultrasound diagnosis apparatus 100 may display the first elasticity image and the first ROI corresponding to the first elasticity value (S360).

For example, the ultrasound diagnosis apparatus 100 may display an indicator indicating the first ROI in the first elasticity image.

Figure 4A:
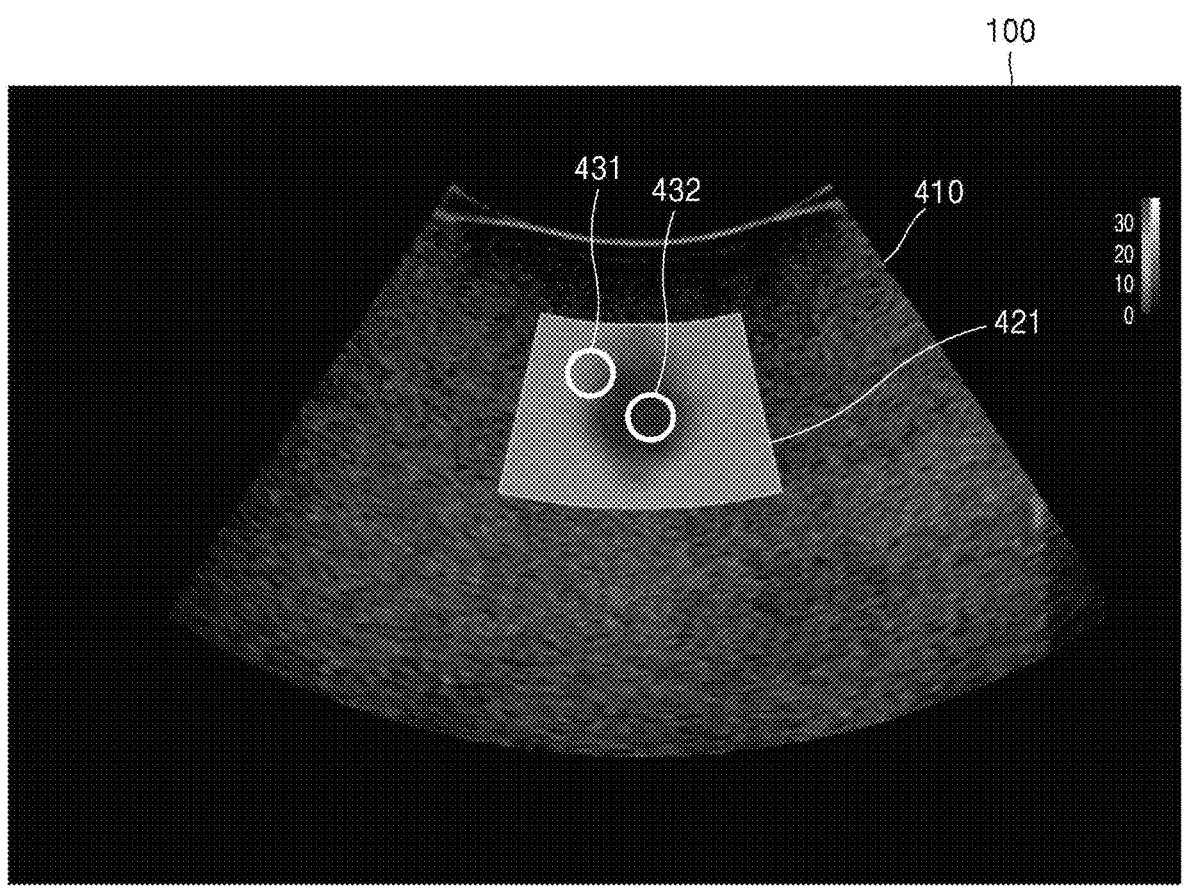
FIGS. 4A and 4B are reference diagrams for describing a method by which an ultrasound diagnosis apparatus acquires a plurality of elasticity values, according to an embodiment.
Figure 4B:
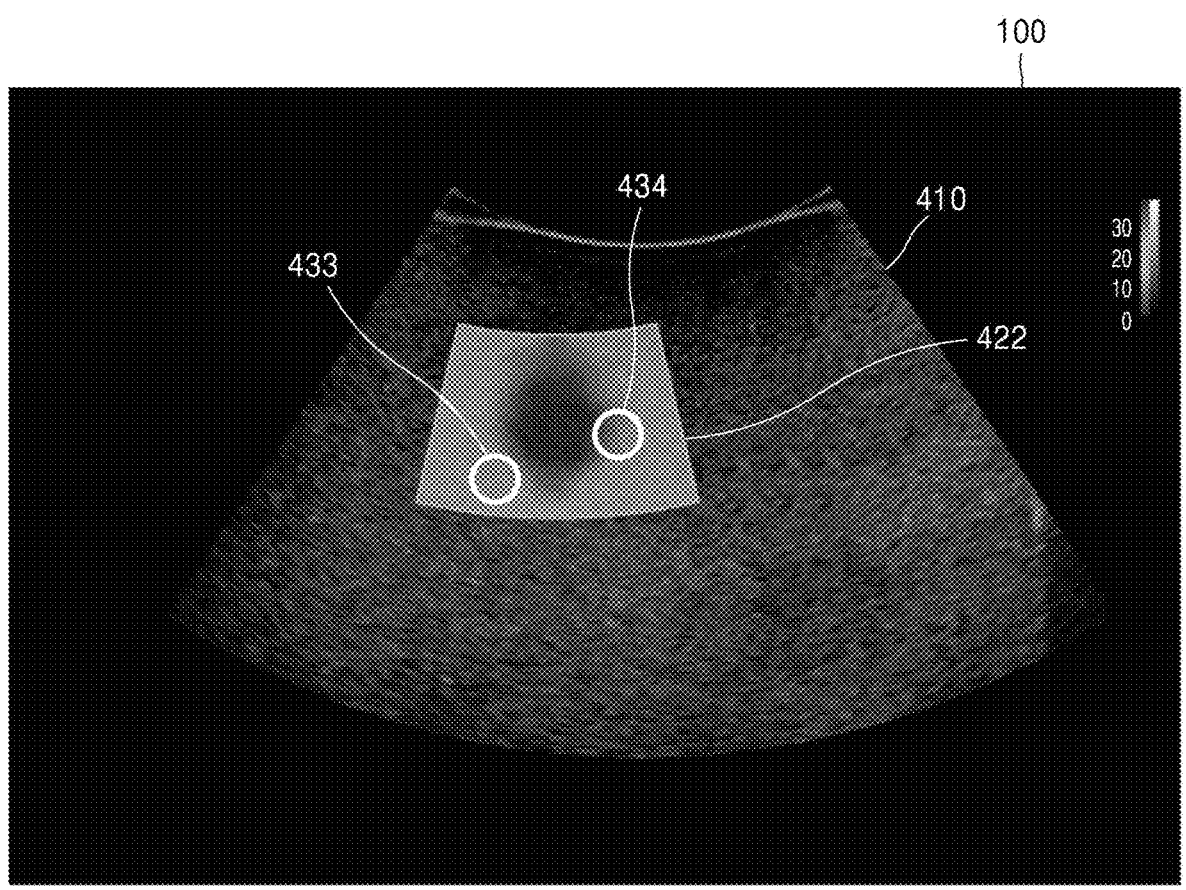

FIGS. 4A and 4B are reference diagrams for describing a method by which the ultrasound diagnosis apparatus 100 acquires a plurality of elasticity values, according to an embodiment.

Referring to FIG. 4A, according to an embodiment, the ultrasound diagnosis apparatus 100 may display an elasticity image (i.e., a first elasticity image 421) showing a first area of an object to overlap a B-mode image 410 of the object. According to an embodiment, the first elasticity image 421 may be an image displayed in different colors according to elasticity values corresponding to a plurality of points included in the first area. For example, a point such as a tumor that is hard and has a low elasticity value may appear red while a point that is relatively soft tissue and has a high elasticity value may appear blue.

According to an embodiment, the ultrasound diagnosis apparatus 100 may determine, in the first area, first and second ROIs 431 and 432 where elasticity values are to be acquired. For example, the ultrasound diagnosis apparatus 100 may set positions, sizes, shapes, etc., of the first and second ROIs 431 and 432 based on a user input. In this case, the ultrasound diagnosis apparatus 100 may display the determined first and second ROIs 431 and 432 to be distinguished from the other regions in the first elasticity image 421 by using a marker or a graphic indicator including a geometric shape such as a circle or a box shape, an arrow, a text, etc.

According to an embodiment, when the first and second ROIs 431 and 432 are determined, the ultrasound diagnosis apparatus 100 may acquire an elasticity value corresponding to the first ROI 431. For example, the ultrasound diagnosis apparatus 100 may calculate, based on elasticity data (first elasticity data) with respect to the first area, a first elasticity value corresponding to the first ROI 431 and a second elasticity value corresponding to the second ROI 432. The first elasticity value may include a mean value, a standard deviation, and a confidence level of elasticity values respectively corresponding to a plurality of points included in the first ROI 431. Furthermore, the second elasticity value may include a mean value, a standard deviation, and a confidence level of elasticity values corresponding to a plurality of points included in the second ROI 432.

According to an embodiment, the ultrasound diagnosis apparatus 100 may store the first elasticity value in correspondence with the first elasticity image 421 and a first indicator indicating the first ROI 431. In addition, the second elasticity value may be stored in correspondence with the first elasticity image 421 and a second indicator indicating the second ROI 432.

Referring to FIG. 4B, according to an embodiment, the ultrasound diagnosis apparatus 100 may display an elasticity image (i.e., a second elasticity image 422) showing a second area of the object to overlap the B-mode image 410 of the object. The second area may be an area having at least one of a position, a size, and a shape that is different from that of the first area, and the second elasticity image 422 may be an image displayed in different colors according to elasticity values corresponding to a plurality of points included in the second area.

The ultrasound diagnosis apparatus 100 may determine, in the second area, third and fourth ROIs 433 and 434 where elasticity values are to be acquired. For example, the ultrasound diagnosis apparatus 100 may set positions, sizes, shapes, etc., of the third and fourth ROIs 433 and 434 based on a user input. In this case, the ultrasound diagnosis apparatus 100 may display the determined third and fourth ROIs 433 and 434 to be distinguished from the other regions in the second elasticity image 422 by using a marker or a graphic indicator including a geometric shape such as a circle or a box shape, an arrow, a text, etc.

According to an embodiment, when the third and fourth ROIs 433 and 434 are determined, the ultrasound diagnosis apparatus 100 may acquire an elasticity value corresponding to the third ROI 433. For example, the ultrasound diagnosis apparatus 100 may calculate, based on elasticity data (second elasticity data) with respect to the second area, a third elasticity value corresponding to the third ROI 433 and a fourth elasticity value corresponding to the fourth ROI 434. The third elasticity value may include a mean value, a standard deviation, and a confidence level of elasticity values respectively corresponding to a plurality of points included in the third ROI 433. Furthermore, the fourth elasticity value may include a mean value, a standard deviation, and a confidence level of elasticity values respectively corresponding to a plurality of points included in the fourth ROI 434.

According to an embodiment, the ultrasound diagnosis apparatus 100 may store the third elasticity value in correspondence with the second elasticity image 422 and a third indicator indicating the third ROI 433. Furthermore, the fourth elasticity value may be stored in correspondence with the second elasticity image 422 and a fourth indicator indicating the fourth ROI 434.

Figure 5B:
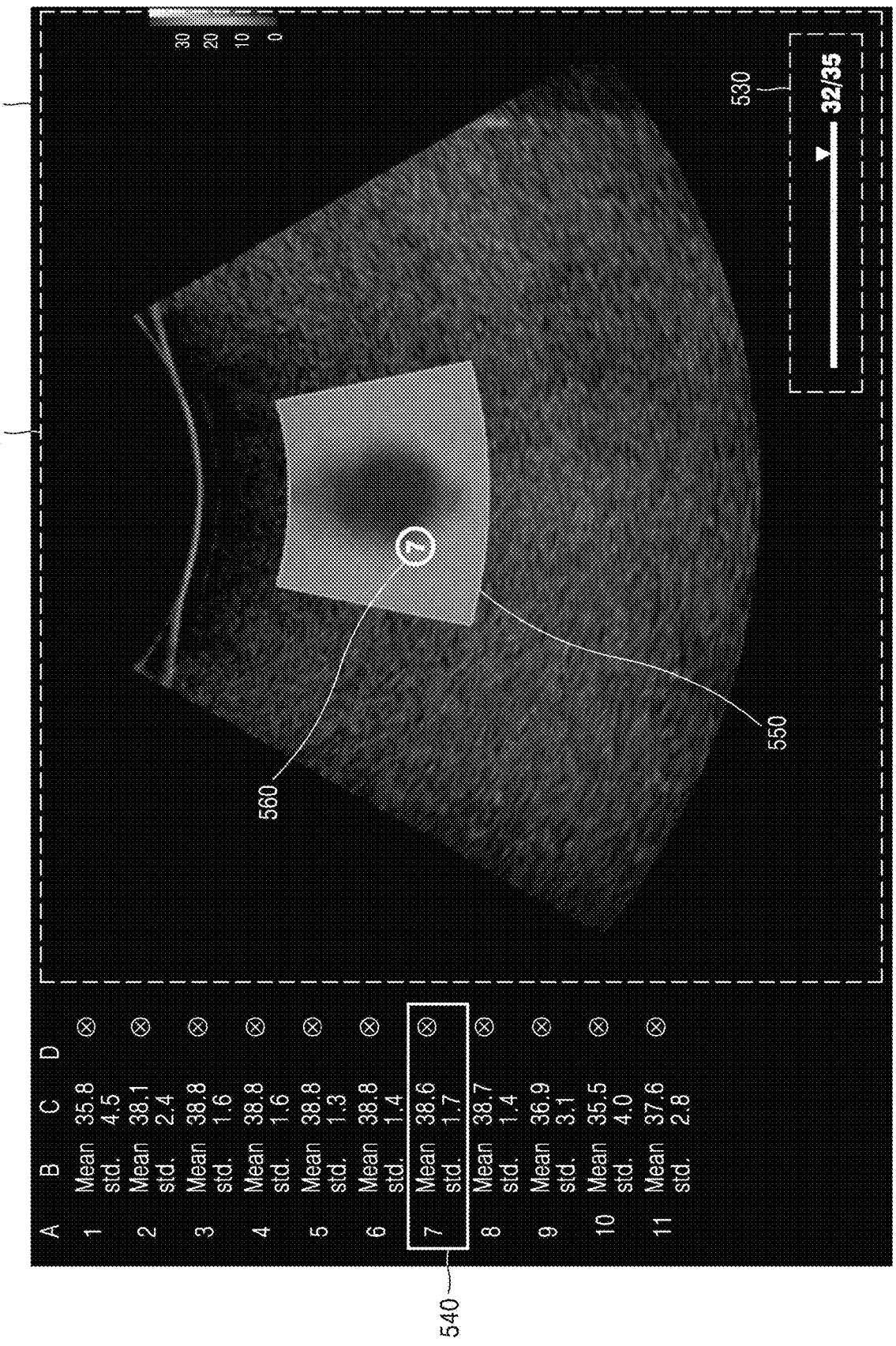
Figure 5C:
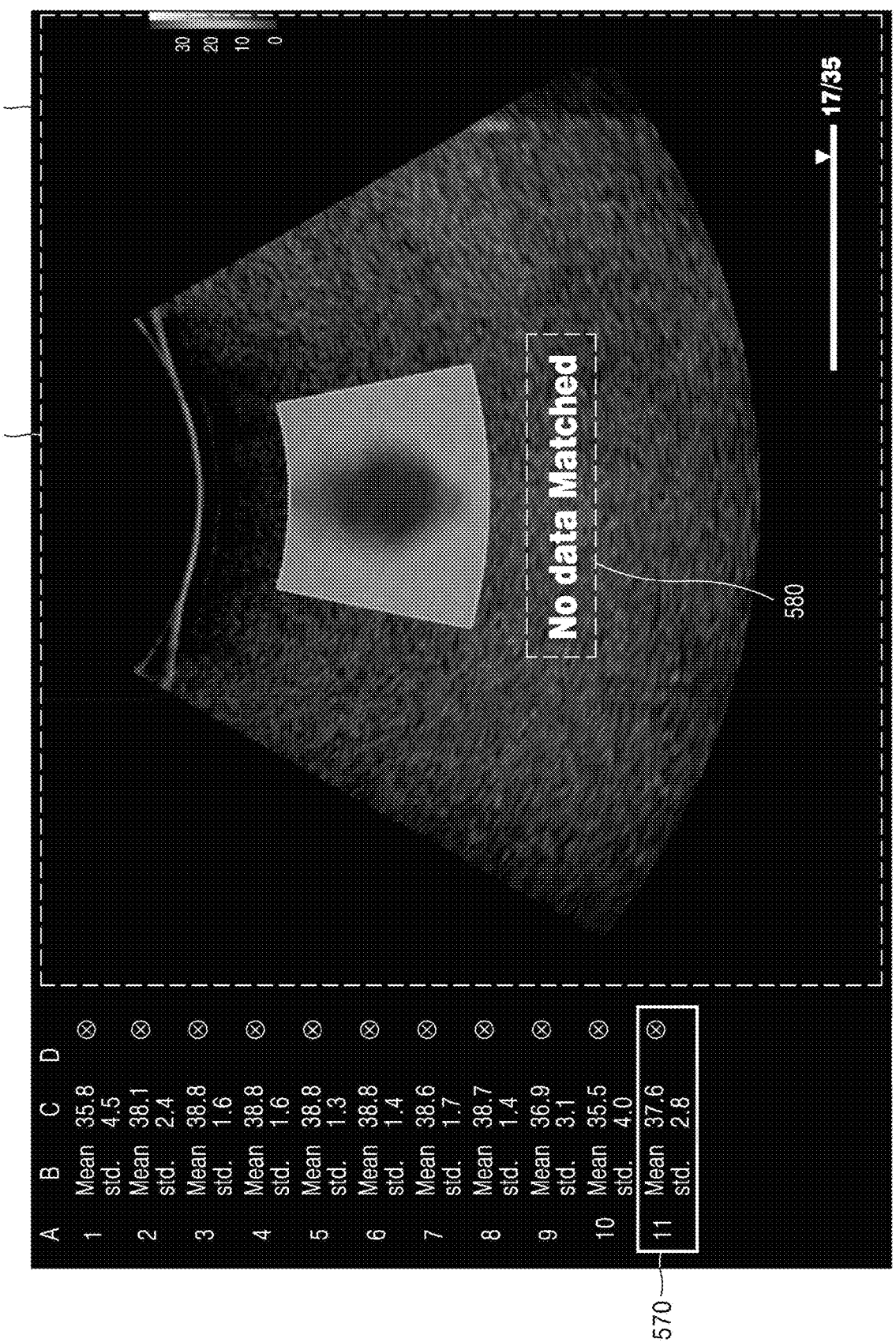

FIGS. 5A through 5C are reference diagrams for describing a method by which the ultrasound diagnosis apparatus 100 provides an elasticity value and an elasticity image corresponding to the elasticity value, according to an embodiment.

Referring to FIG. 5A, according to an embodiment, the ultrasound diagnosis apparatus 100 may display a plurality of acquired elasticity values. Descriptions of a method of acquiring a plurality of elasticity values are already provided above with respect to FIGS. 4A and 4B, and thus, are not repeated below.

Referring to FIG. 5A, according to an embodiment, the ultrasound diagnosis apparatus 100 may display the plurality of elasticity values as a list. For example, the ultrasound diagnosis apparatus 100 may display an elasticity value list 510 including items respectively corresponding to the elasticity values in a first region 501 of a display.

Furthermore, an elasticity image 521 may be displayed in a second region 502 of the display. The elasticity image 521 displayed in the second region 502 may be a live image or a last acquired elasticity image. Alternatively, the elasticity image 521 may be an elasticity image corresponding to one of the elasticity values, but is not limited thereto.

Furthermore, when the elasticity image 502 displayed in the second region 502 is one of the prestored elasticity images, the ultrasound diagnosis apparatus 100 may display a slide bar 530 showing what numberth image is the elasticity image 502 displayed in the second region 502 among the prestored elasticity images. For example, the elasticity image 502 may be stored in the ultrasound diagnosis apparatus 100 in the order that it is acquired, and the slide bar 530 may indicate that the elasticity image 502 displayed in the second region 502 is the 17th elasticity image among 35 prestored elasticity images.

According to an embodiment, the ultrasound diagnosis apparatus 100 may receive, via a user input interface, an input for selecting one of a plurality of elasticity values included in the list 510 through a user input unit.

Referring to FIG. 5B, when any one of the elasticity values included in the elasticity value list 510 is selected, the ultrasound diagnosis apparatus 100 may display a selected item, i.e., a first item 540 corresponding to the selected elasticity value, to be distinguished from other items. For example, a border of the first item 540 may be bolded, or the first item 540 may be highlighted. However, embodiments are not limited thereto.

Furthermore, the ultrasound diagnosis apparatus 100 may display an elasticity image 550 corresponding to the selected elasticity value in the second region 502 of the display. For example, when a third elasticity value is selected, the second elasticity image 550 corresponding to the third elasticity value may be displayed. Furthermore, a third indicator 560 indicating a third ROI corresponding to the third elasticity value may be displayed in the second elasticity image 550. In this case, the second elasticity image 550 may be an elasticity image in which the third ROI is set when the third elasticity value corresponding to the third ROI is acquired. According to an embodiment, after the third elasticity value is acquired, the ultrasound diagnosis apparatus 100 may store the third elasticity value in correspondence with the second elasticity image 550 corresponding to the third elasticity value and the third indicator 560 indicating the third ROI.

An index of the third elasticity value may also be displayed in the third indicator 560. For example, when the index of the third elasticity value is '7', '7' may be displayed in the third indicator 560.

Furthermore, as the second elasticity image 550 is displayed, the slide bar 530 may indicate that the second elasticity image 550 is the 32nd elasticity image among the 35 prestored elasticity images.

Accordingly, the user may easily identify a position of an ROI corresponding to an elasticity value, which is selected via an input for selecting an elasticity value from the elasticity value list 510, as well as an elasticity image corresponding to the selected elasticity value, without having to individually examine a plurality of prestored elasticity images.

Referring to FIG. 5C, according to an embodiment, when an elasticity image corresponding to an elasticity value (i.e., a second item 570) selected from the elasticity value list 510 is not stored in the ultrasound diagnosis apparatus 100, the ultrasound diagnosis apparatus 100 may display a message 580 indicating that there is no corresponding elasticity image.

Furthermore, when an elasticity value (item) is selected from the elasticity value list 510, the ultrasound diagnosis apparatus 100 may display the selected item differently according to whether its corresponding elasticity image exists (is stored). For example, as shown in FIG. 5B, when the elasticity value (i.e., the first item 540) having a corresponding elasticity image is selected, the border of the first item is bolded or highlighted in a first color. On the other hand, as shown in FIG. 5C, when the elasticity value (i.e., the second item 570) having no corresponding elasticity image is selected, a border of the second item 570 may be bolded or highlighted in a second color.

Alternatively, according to an embodiment, the ultrasound diagnosis apparatus 100 may display items that are not selected from the elasticity value list 510 to be distinguished according to whether their corresponding elasticity images are stored. For example, an item for which a corresponding elasticity image is not stored may be displayed as an inactive state to prevent the item from being selected.

Figure 6:
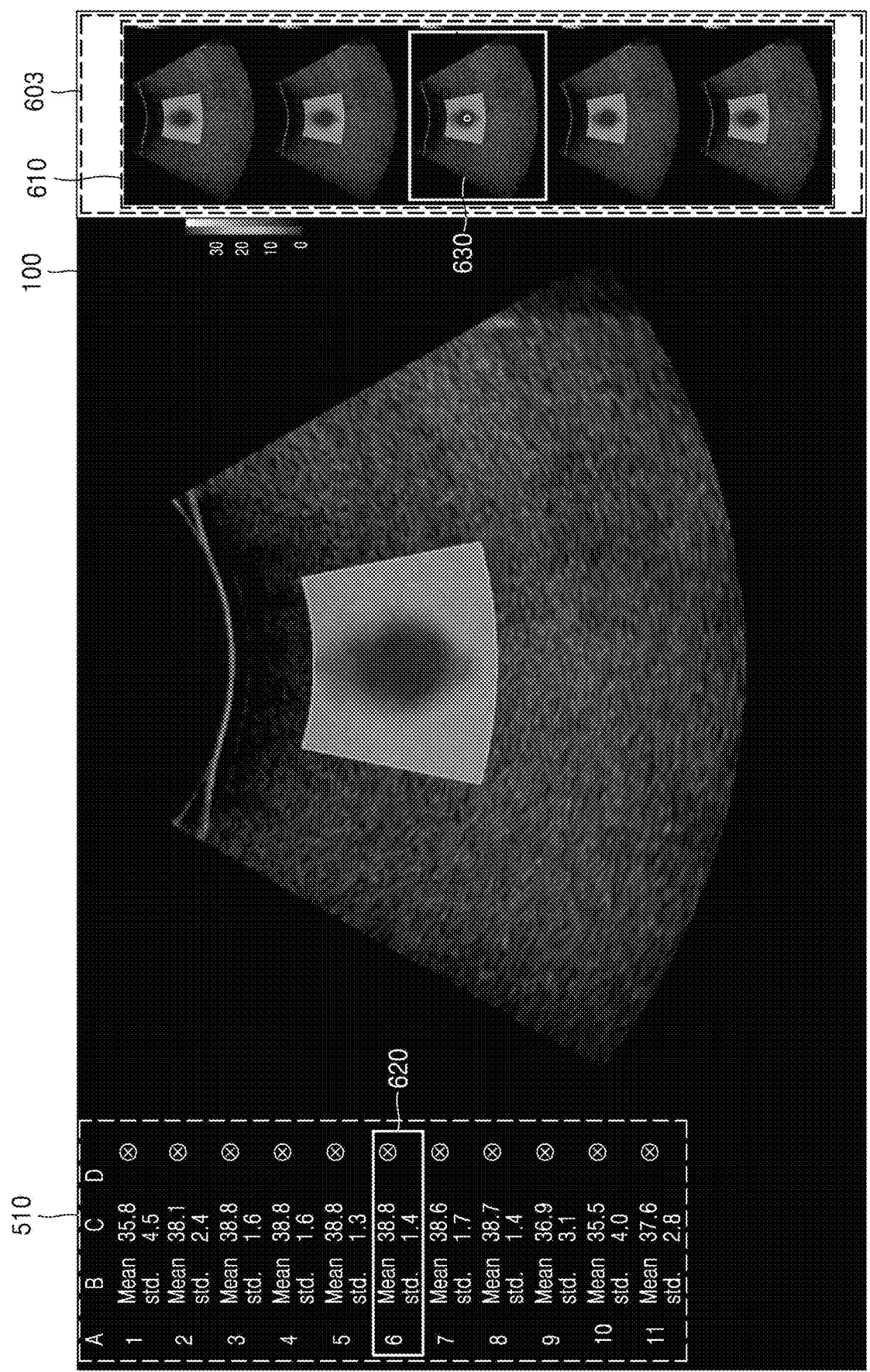
FIG. 6 is a reference diagram for describing a method by which an ultrasound diagnosis apparatus provides an elasticity value and an elasticity image corresponding to the elasticity value, according to an embodiment.

FIG. 6 is a reference diagram for describing a method by which the ultrasound diagnosis apparatus 100 provides an elasticity value and an elasticity image corresponding to the elasticity value, according to an embodiment.

Referring to FIG. 6, according to an embodiment, the ultrasound diagnosis apparatus 100 may display a plurality of acquired elasticity values as a list. Descriptions of a method of displaying a plurality of elasticity values as a list are already provided above with respect to FIG. 5A, and thus, are not repeated below.

Furthermore, the ultrasound diagnosis apparatus 100 may display, in a third region 603 of a display, a thumbnail list 610 including thumbnail images respectively corresponding to a plurality of prestored elasticity images. For example, the prestored elasticity images may include some of the elasticity images corresponding to the acquired elasticity values.

According to an embodiment, the ultrasound diagnosis apparatus 100 may receive, via a user input interface, an input for selecting one of the elasticity values included in a list 510.

When one of elasticity values included in the list 510 is selected, the ultrasound diagnosis apparatus 100 may display a thumbnail image corresponding to the selected elasticity value from among the thumbnail images included in the thumbnail list 610 such that the thumbnail image is distinguished from other thumbnail images. For example, when a first elasticity value 620 acquired based on first elasticity data is selected, a thumbnail image 630 of a first elasticity image corresponding to the first elasticity value 620 from among the thumbnail images may be displayed in such a manner as to be distinguished from other thumbnail images. For example, a border of the thumbnail image 630 of the first elasticity image may be bolded or highlighted. However, embodiments are not limited thereto.

Figure 7:
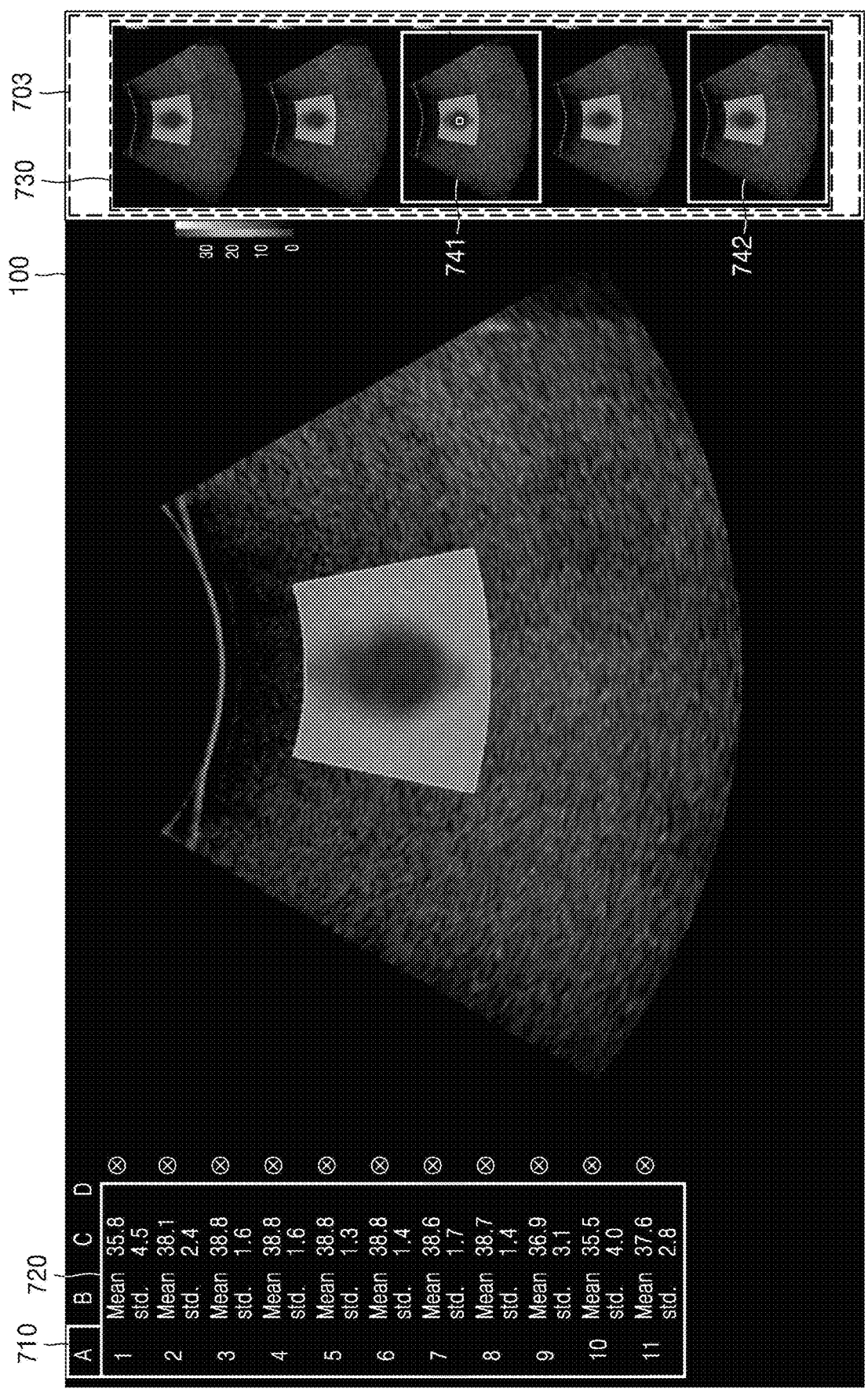
FIG. 7 is a reference diagram for describing a method by which an ultrasound diagnosis apparatus provides an elasticity value and an elasticity image corresponding to the elasticity value for each group, according to an embodiment.

FIG. 7 is a reference diagram for describing a method by which the ultrasound diagnosis apparatus 100 provides an elasticity value and an elasticity image corresponding to the elasticity value for each group, according to an embodiment.

Referring to FIG. 7, according to an embodiment, the ultrasound diagnosis apparatus 100 may classify a plurality of acquired elasticity values into a plurality of groups. For example, elasticity values acquired based on first elasticity data may be classified as a first group while elasticity values acquired based on second elasticity data may be classified as a second group. However, embodiments are not limited thereto, and a plurality of elasticity values may be classified into a plurality of groups according to various criteria.

Furthermore, the ultrasound diagnosis apparatus 100 may display a plurality of elasticity values classified as a first group as a first list while displaying a plurality of elasticity values classified as a second group as a second list.

According to an embodiment, when a user input for selecting one of a plurality of groups is received, the ultrasound diagnosis apparatus 100 may display a list corresponding to the selected group. For example, FIG. 7 shows a state in which a first list 720 is displayed when a first group 710 is selected.

Furthermore, the ultrasound diagnosis apparatus 100 may display, in a third region 703 of a display, a thumbnail list 730 including a plurality of thumbnail images respectively corresponding to a plurality of prestored elasticity images. For example, the prestored elasticity images may include some of the elasticity images corresponding to a plurality of elasticity values.

According to an embodiment, when a user input for selecting one of the groups is received, the ultrasound diagnosis apparatus 100 may display thumbnail images corresponding to the selected group from among the thumbnail images included in the thumbnail list 730 such that the thumbnail images are distinguished from other thumbnail images. For example, thumbnail images (i.e., first thumbnail images 741 and 742) of elasticity images corresponding to the elasticity values included in the first group 710 may be displayed in such a manner as to be distinguished from other thumbnail images. Borders of the first thumbnail images 741 and 742 may be bolded or highlighted. However, embodiments are not limited thereto.

Figure 8:
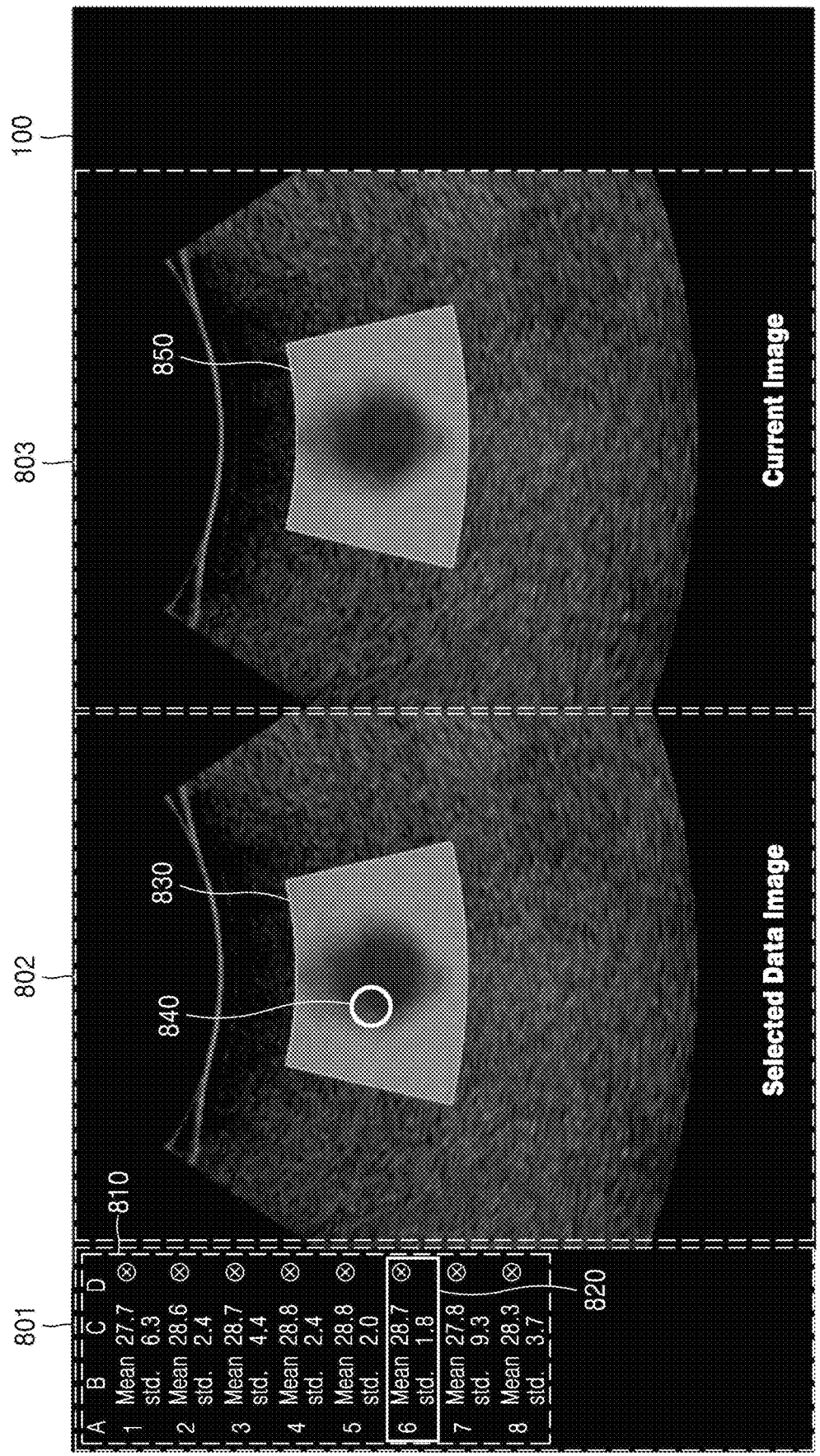
FIG. 8 is a reference diagram for describing a method by which an ultrasound diagnosis apparatus provides an elasticity value and an elasticity image corresponding to the elasticity value, according to an embodiment.

FIG. 8 is a reference diagram for describing a method by which the ultrasound diagnosis apparatus 100 provides an elasticity value and an elasticity image corresponding to the elasticity value, according to an embodiment.

Referring to FIG. 8, according to an embodiment, the ultrasound diagnosis apparatus 100 may display a list 810 including a plurality of acquired elasticity values in a first region 801 of a display. When one of the elasticity values included in the list 810 is selected, the ultrasound diagnosis apparatus 100 may display a selected item 820 to be distinguished from other items. For example, the border of the selected item 820 may be displayed in bold.

Furthermore, the ultrasound diagnosis apparatus 100 may display an elasticity image corresponding to the selected elasticity value in a second region 802 of the display. For example, when a third elasticity value is selected, a second elasticity image 830 corresponding to the third elasticity value may be displayed. Furthermore, a third indicator 840 indicating a third ROI corresponding to the third elasticity value may be displayed in the second elasticity image 830. Here, the second elasticity image 830 may be an elasticity image in which the third ROI is set when the third elasticity value corresponding to the third ROI is acquired.

Furthermore, the ultrasound diagnosis apparatus 100 may display, in a third region 803 of the display, an elasticity image 850 generated based on elasticity data acquired in real time as a live image.

Figure 9:
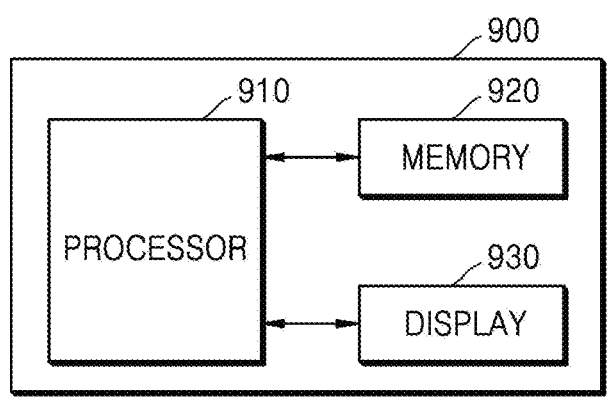
FIG. 9 is a block diagram of a configuration of an ultrasound diagnosis apparatus according to an embodiment.

FIG. 9 is a block diagram of a configuration of an ultrasound diagnosis apparatus 900 according to an embodiment.

Referring to FIG. 9, according to an embodiment, the ultrasound diagnosis apparatus 900 may include a processor 910, a memory 920, and a display 930.

The processor 910 of FIG. 9 may correspond to at least one or a combination of the ultrasound transceiver 110, the controller 120, and the image processor 130 described with reference to FIG. 1, and the display 930 may correspond to the display 140 of FIG. 1. Furthermore, according to an embodiment, some of the components of the ultrasound diagnosis apparatus 100 of FIG. 1 may be included in the ultrasound diagnosis apparatus 900 of FIG. 9.

According to an embodiment, the processor 910 may control all operations of the ultrasound diagnosis apparatus 900. According to an embodiment, the processor 910 may execute one or more programs stored in the memory 920.

According to an embodiment, the memory 920 may store various data, programs, or applications for driving and controlling the ultrasound diagnosis apparatus 900. A program stored in the memory 920 may include one or more instructions. Programs (one or more instructions) or applications stored in the memory 920 may be executed by the processor 910.

According to an embodiment, the processor 910 may transmit ultrasound signals to an object, acquire ultrasound data based on echo signals received from the object, and generate a B-mode ultrasound image of the object based on the ultrasound data. Furthermore, when a first area where elasticity data is to be acquired is set based on the B-mode ultrasound image, the processor 910 may acquire first elasticity data with respect to the first area. The processor 910 may transmit an ultrasonic signal to the object such that a shear wave may be induced in tissue of the object to cause a displacement of the tissue (understandable?), detect a shear wave displacement caused by the induced shear wave, and acquire elasticity data with respect to the object.

The processor 910 may generate a first elasticity image based on the first elasticity data, and control the display 930 to display the first elasticity image.

When an ROI where an elasticity value is to be acquired is determined in the first area based on the first elasticity image, the processor 910 may acquire an elasticity value corresponding to the ROI based on the first elasticity data. For example, when a first ROI is set in the first area, the processor 910 may acquire a first elasticity value corresponding to the first ROI by calculating a mean value, a standard deviation, and a confidence level of elasticity values corresponding to a plurality of points included in the first ROI. Furthermore, when a second ROI different from the first ROI is set in the first area, the processor 910 may acquire a second elasticity value corresponding to the second ROI by calculating a mean value, a standard deviation, and a confidence level of elasticity values corresponding to a plurality of points included in the second ROI. In this way, the processor 910 may acquire elasticity values respectively corresponding to a plurality of ROIs in the first area.

After the first elasticity value is acquired, the processor 910 may store the first elasticity value in the memory 920 in correspondence with the first elasticity image corresponding to the first elasticity value and an indicator indicating the first ROI. Furthermore, after the second elasticity value is acquired, the second elasticity value may be stored in the memory 920 in correspondence with the first elasticity image corresponding to the second elasticity value and an indicator indicating the second ROI.

In addition, the processor 910 may control the display 930 to display the acquired plurality of elasticity values as a list, and when one of the plurality of elasticity values is selected, the processor 910 may control the display 930 to display an elasticity image corresponding to the selected elasticity value and an indicator indicating an ROI corresponding thereto.

According to an embodiment, the display 930 may display an operation state of the ultrasound diagnosis apparatus 100, an ultrasound image, and a user interface, etc. The display 930 may include one or more display panels according to embodiments and may be formed as a touch screen.

According to an embodiment, the display 930 may display a B-mode ultrasound image of the object and display an elasticity image of a region of the object to overlap the B-mode ultrasound image. Furthermore, the display 930 may display in the elasticity image an indicator (grammar?) indicating an ROI where an elasticity value is to be acquired.

According to an embodiment, the display 930 may display a plurality of acquired elasticity values as a list, and when one of the acquired elasticity values is selected, the display 930 may display an elasticity image corresponding to the selected elasticity value and an indicator indicating a ROI corresponding thereto. In addition, the display 930 may display, in the list, an elasticity value having a corresponding elasticity image (understandable?) to be distinguished from an elasticity value having a corresponding elasticity image.

Block diagrams of the ultrasound diagnosis apparatuses 100 and 900 of FIGS. 1 and 9 may be provided for illustration of embodiments. Each of the components in the block diagram may be integrated, added, or omitted according to the specification of the ultrasound diagnosis apparatus 100 or 900 that is actually implemented. In other words, two or more components may be combined into a single component, or a single component may be split into two or more components if necessary. Functions performed in each block are intended to describe embodiments, and a specific operation or apparatus related to the functions does not limit the scope of the disclosure.

An operating method of an ultrasound diagnosis apparatus according to an embodiment may be implemented in the form of program instructions that may be performed by various types of computers and may be recorded on computer-readable recording media. The computer-readable recording media may include program instructions, data files, data structures, etc. either alone or in combination. The program instructions recorded on the computer-readable recording media may be designed and configured specially for the disclosure or may be known to and be usable by those skilled in the art of computer software. Examples of the computer-readable recording media include magnetic media such as hard disks, floppy disks, and magnetic tape, optical media such as compact disk read-only memory (CD-ROM) and digital versatile disks (DVDs), magneto-optical media such as floptical disks, and hardware devices that are specially configured to store and perform program instructions, such as ROM, random access memory (RAM), flash memory, etc. Examples of program instructions include not only machine code such as that created by a compiler but also higher level language code that may be executed by a computer using an interpreter or the like.

In addition, ultrasound diagnosis apparatuses and operating methods thereof according to embodiments of the disclosure may be included in a computer program product when provided. The computer program product may be traded, as a commodity, between a seller and a buyer.

The computer program product may include a software program and a computer-readable storage medium having stored thereon the software program. For example, the computer program product may include a product (e.g. a downloadable application) in the form of a software program electronically distributed by a manufacturer of an ultrasound diagnosis apparatus or through an electronic market (e.g., Google Play Store™ and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a client device, the computer program product may include a storage medium of the server or a storage medium of the client device. Alternatively, in a case where a third device (e.g., a smartphone) is connected to the server or client device through a communication network, the computer program product may include a storage medium of the third device. Alternatively, the computer program product may include a software program itself that is transmitted from the server to the client device or the third device or that is transmitted from the third device to the client device.

In this case, one of the server, the client device, and the third device may execute the computer program product to perform methods according to embodiments of the disclosure. Alternatively, two or more of the server, the client device, and the third device may execute the computer program product to perform the methods according to the embodiments in a distributed manner.

For example, the server (e.g., a cloud server, an artificial intelligence server, or the like) may run the computer program product stored therein to control the client device communicating with the server to perform the methods according to the embodiments of the disclosure.

According to an embodiment, an ultrasound diagnosis apparatus may provide, when an elasticity value is selected, an elasticity image and an ROI corresponding to the selected elasticity value, thereby allowing the user to easily identify a position of the ROI and the elasticity image corresponding to the selected elasticity value without needing to individually examine a plurality of elasticity images.

While one or more embodiments have been particularly described with reference to the figures, it will be understood by those of ordinary skill in the art that the embodiments are not to be construed as limiting the scope of the disclosure and various changes and modifications in form and details based on the basic concept of the disclosure also fall within the scope as defined by the following claims.

What is claimed is:

1. An ultrasound diagnosis apparatus comprising:
a display configured to display a B-mode ultrasound image of an object;
a probe configured to transmit and receive ultrasound signals to a first area of the object to acquire first elasticity data when the first area of the object is set in the B-mode ultrasound image, and transmit and receive the ultrasound signals to a second area of the object to acquire second elasticity data when the second area of the object is set in the B-mode ultrasound image, wherein the second area of the object has at least one of a position, a size, and a shape that is different from that of the first area of the object;
at least one image processor configured to generate a first elasticity image based on the first elasticity data and generate a second elasticity image based on the second elasticity data;
at least one memory storing one or more instructions; and
at least one processor configured to execute the one or more instructions to:
acquire the first elasticity data with respect to the first area of the object and acquire the second elasticity data with respect to the second area of the object, based on a shear wave displacement caused by the ultrasound signals;
acquire, based on the first elasticity data, a first elasticity value corresponding to a first region of interest in the first area of the object;
acquire, based on the second elasticity data, a second elasticity value corresponding to a second region of interest in the second area of the object;
store the first elasticity value in association with the first elasticity image and the first region of interest, and the second elasticity value in association with the second elasticity image and the second region of interest in the at least one memory;
control the display to display an elasticity value list comprising a plurality of elasticity values comprising the first elasticity value and the second elasticity value, in a first region of the display;
receive a user input for selecting one of the plurality of elasticity values in the elasticity value list;
in response to the first elasticity value being selected from the elasticity value list, control the display to display the first elasticity value as distinguished from the plurality of elasticity values in the elasticity value list and display the first elasticity image having a first indicator indicating the first region of interest in a second region of the display; and
in response to the second elasticity value being selected from the elasticity value list, control the display to display the second elasticity value as distinguished from the plurality of elasticity values in the elasticity value list and display the second elasticity image having a second indicator indicating the second region of interest in the second region of the display.

2. The ultrasound diagnosis apparatus of claim 1, wherein the at least one processor is further configured to execute the one or more instructions to:
acquire, based on the first elasticity data, a third elasticity value corresponding to a third region of interest in the first area of the object;
acquire, based on the second elasticity data, a fourth elasticity value corresponding to a fourth region of interest in the second area of the object;
determine the first elasticity value and the third elasticity value acquired based on the first elasticity data as a first group;
determine the second elasticity value and the fourth elasticity value acquired based on the second elasticity data as a second group; and
control the display to display the elasticity values for each of the first group and the second group.

3. The ultrasound diagnosis apparatus of claim 2, wherein the at least one processor is further configured to execute the one or more instructions to:
in response to the first group being selected, control the display to display the first elasticity image corresponding to the first group as distinguished from the second elasticity image corresponding to the second group.

4. The ultrasound diagnosis apparatus of claim 3, wherein the at least one processor is further configured to execute the one or more instructions to:
control the display to display a thumbnail list including the first elasticity image corresponding to the first group and the second elasticity image corresponding to the second group; and
in response to the first group being selected, control the display to highlight and display the first elasticity image in the thumbnail list.

5. The ultrasound diagnosis apparatus of claim 2,
wherein the plurality of elasticity values further comprises a fifth elasticity value, and
wherein the at least one processor is further configured to execute the one or more instructions to:
in response to the fifth elasticity value being selected from the elasticity value list and an elasticity image corresponding to the fifth elasticity value being not stored, control the display to display a message indicating that there is no corresponding elasticity image.

6. The ultrasound diagnosis apparatus of claim 5, wherein the at least one processor is further configured to execute the one or more instructions to:
control the display to display, in the elasticity value list, an elasticity value for which a corresponding elasticity image is stored as distinguished from an elasticity value for which a corresponding elasticity image is not stored.

7. An operating method of an ultrasound diagnosis apparatus, comprising:
displaying a B-mode ultrasound image of an object;
transmitting and receiving ultrasound signals to a first area of the object to acquire first elasticity data when the first area of the object is set in the B-mode ultrasound image;
transmitting and receiving the ultrasound signals to a second area of the object to acquire second elasticity data when the second area of the object is set in the B-mode ultrasound image, wherein the second area of the object has at least one of a position, a size, and a shape that is different from that of the first area of the object;
acquiring the first elasticity data with respect to the first area of the object based on a shear wave displacement caused by the ultrasound signals;
acquiring the second elasticity data with respect to the second area of the object based on the shear wave displacement caused by the ultrasound signals;
acquiring, based on the first elasticity data, a first elasticity value corresponding to a first region of interest in the first area of the object;
acquiring, based on the second elasticity data, a second elasticity value corresponding to a second region of interest in the second area of the object;
generating a first elasticity image based on the first elasticity data;
generating a second elasticity image based on the second elasticity data;
storing the first elasticity value in association with the first elasticity image and the first region of interest, and the second elasticity value in association with the second elasticity image and the second region of interest in at least one memory;
displaying an elasticity value list comprising a plurality of elasticity values comprising the first elasticity value and the second elasticity value in a first region of a display;
receiving a user input for selecting one of the plurality of elasticity values in the elasticity value list;
in response to the first elasticity value being selected from the elasticity value list, displaying the first elasticity value as distinguished from the plurality of elasticity values in the elasticity value list and displaying the first elasticity image having a first indicator indicating the first region of interest in a second region of the display; and
in response to the second elasticity value being selected from the elasticity value list, displaying the second elasticity value as distinguished from the plurality of elasticity values in the elasticity value list and displaying the second elasticity image having a second indicator indicating the second region of interest in the second region of the display.

8. The operating method of claim 7, further comprising:
acquiring, based on the first elasticity data, a third elasticity value corresponding to a third region of interest in the first area of the object;
acquiring, based on the second elasticity data, a fourth elasticity value corresponding to a fourth region of interest in the second area of the object;
determining the first elasticity value and the third elasticity value acquired based on the first elasticity data as a first group; and
determining the second elasticity value and the fourth elasticity value acquired based on the second elasticity data as a second group,
wherein the displaying of the elasticity value list comprises displaying the elasticity values for each of the first group and the second group.

9. The operating method of claim 8, further comprising:
in response to the first group being selected, displaying the first elasticity image corresponding to the first group as distinguished from the second elasticity image corresponding to the second group.

10. The operating method of claim 9, further comprising:
displaying a thumbnail list including the first elasticity image corresponding to the first group and the second elasticity image corresponding to the second group,
wherein the displaying of the first elasticity image as distinguished from the second elasticity image comprises,
in response to the first group being selected, highlighting and displaying the first elasticity image corresponding to the first group in the thumbnail list.

11. The operating method of claim 8, wherein the plurality of elasticity values further comprises a fifth elasticity value, the operating method further comprising:
in response to the fifth elasticity value being selected from the elasticity value list and an elasticity image corresponding to the fifth elasticity value being not stored, displaying a message indicating that there is no corresponding elasticity image.

12. The operating method of claim 11, further comprising:
displaying, in the elasticity value list, an elasticity value for which the corresponding elasticity image is stored as distinguished from an elasticity value for which the corresponding elasticity image is not stored.

13. A non-transitory computer-readable recording medium having recorded thereon a program for performing an operating method of an ultrasound diagnosis apparatus, the operating method comprising:
displaying a B-mode ultrasound image of an object;
transmitting and receiving ultrasound signals to a first area of the object to acquire first elasticity data when the first area of the object is set in the B-mode ultrasound image;
transmitting and receiving the ultrasound signals to a second area of the object to acquire second elasticity data when the second area of the object is set in the B-mode ultrasound image, wherein the second area of the object has at least one of a position, a size, and a shape that is different from that of the first area of the object;
acquiring the first elasticity data with respect to the first area of the object based on a shear wave displacement caused by the ultrasound signals;
acquiring the second elasticity data with respect to the second area of the object based on the shear wave displacement caused by the ultrasound signals;

acquiring, based on the first elasticity data, a first elasticity value corresponding to a first region of interest in the first area of the object;

acquiring, based on the second elasticity data, a second elasticity value corresponding to a second region of interest in the second area of the object;

generating a first elasticity image based on the first elasticity data;

generating a second elasticity image based on the second elasticity data;

storing the first elasticity value in association with the first elasticity image and the first region of interest, and the second elasticity value in association with the second elasticity image and the second region of interest in at least one memory;

displaying an elasticity value list comprising a plurality of elasticity values comprising the first elasticity value and the second elasticity value in a first region of a display;

receiving a user input for selecting one of the plurality of elasticity values in the elasticity value list;

in response to the first elasticity value being selected from the elasticity value list, displaying the first elasticity value as distinguished from the plurality of elasticity values in the elasticity value list and displaying the first elasticity image having a first indicator indicating the first region of interest in a second region of the display; and in response to the second elasticity value being selected from the elasticity value list, displaying the second elasticity value as distinguished from the plurality of elasticity values in the elasticity value list and displaying the second elasticity image having a second indicator indicating the second region of interest in the second region of the display.

\* \* \* \* \*